Feb. 15, 1938. M. HARPOLE Plant Pat. 271
PEACH TREE
Filed May 20, 1937
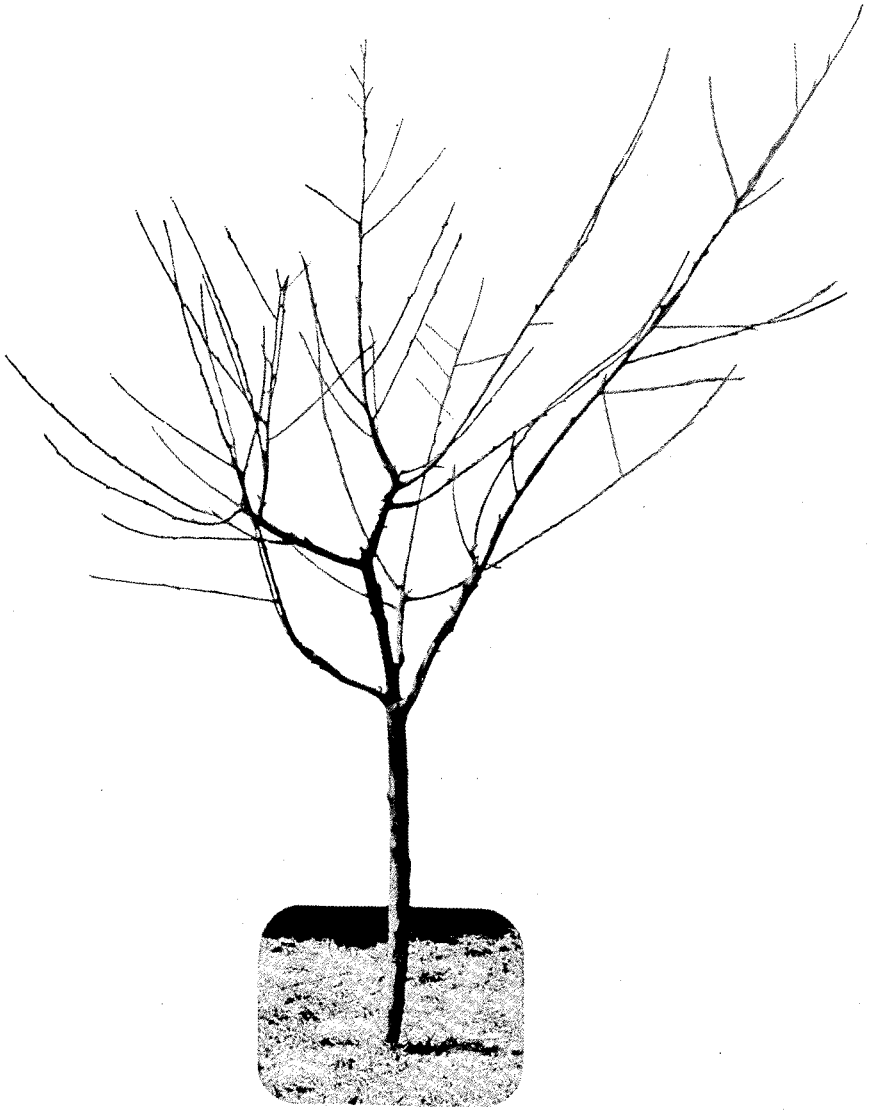
Inventor
Marsh Harpole
By Robert Robb
Attorneys Patented Feb. 15, 1938

Plant Pat. 271

UNITED STATES PATENT OFFICE

271

PEACH TREE

Marsh Harpole, Mount Vernon, Ill., assignor to Stark Bro's Nurseries and Orchards Company, Louisiana, Mo.

Application May 20, 1937, Serial No. 143,828

1 Claim. (Cl. 47—62)

This discovery relates to a new and distinct variety of peach tree, a seedling of unknown parentage, having as its dominating feature unusual hardiness compared with other varieties which most nearly resemble the same grown under comparable conditions.

The original tree of this new variety has bloomed and produced fruit in seasons when all other varieties in the same orchard and grown under comparable conditions had their blossoms completely wiped out and most of the trees of such other varieties were entirely killed.

This same extraordinary hardiness and vigor is manifested in the young trees propagated from the original, as evidenced from the fact that they have withstood temperatures from 17° to 20° below zero, coming through with live buds and blooming in a season when the buds of all other varieties in the same section or locality were killed. Some of these young trees at the age of two years had as many as sixty-five blossoms, which is a record for such a young tree.

In the section of Jefferson County, Illinois, in which these tests occurred, there are grown a large number of varieties of peach trees and the extremely cold winter, during which the tests were conducted, killed all of the blossoms of these other varieties, but failed to hurt the present variety.

This new variety is characterized by other important distinctions, among which may be mentioned the habit of ripening approximately seven to ten days after the well known Elberta grown in the same orchard and under comparable conditions; its distinctive type of spreading growth, strong framework with broad crotches; and the extra dark oily green foliage, differing from most varieties in these respects.

The following is a detail description of the new variety, all color references being in accordance with the Ridgway Color Standard:—

Tree:
- Medium size, vigorous, spreading.
- Medium to dense, round topped.
- Hardy, productive, regular bearer.

Trunk:
- Medium size.
- Medium smoothness.

Branches:
- Medium size, medium smoothness.
- *Color.*—Brown with red on exposed side.
- *Lenticels.*—Medium in number. Large size.

Leaves:
- *Length.*—Five to six inches.
- *Width.*—1¼ to 1¾ inches.
- Ovate to lanceolate, medium thickness.
- Medium green color, smooth.
- *Margin.*—Coarsely serrate.
- *Petiole.*—⅜ inches long, medium thickness.
- *Glands.*—Average number two to three. Alternate, medium size, reniform. Color—red. Position—some on petiole and some on base of leaf.

Stipules—none.

Flower buds:
- Hardy, medium size, medium length.
- Pointed, free, pubescent.

Fruit:

It is of the Elberta type with yellow ground color, almost completely covered with red.

Date ripens for eating from tree—between September 1st and 5th.

*Size.*—Diameter axial—three inches. Transverse in suture plan—three inches. At right angles to suture plane—2¾ inches.

*Form.*—Slightly compressed oblong.

*Suture.*—Distinct, deep.

*Apex.*—Short, pointed.

*Skin.*—Free. Down—moderate.

*Flesh.*—Lemon yellow when in commercial stage, turning to orange yellow when fully matured, with very little red around stone. Surface of pit cavity—mottled red with yellow. Juice—moderate. Texture—firm. Flavor—some acid. Eating quality—the quality of the fruit is good with only a slight suggestion of Elberta bitterness. Quality is better than Elberta.

*Stone.*—The stone is extremely long with an unusual shape. It is very thin and narrow on one side and pointed, having most of the seed bulge on one side and is flat on the other side. Stone is free. Size—very large. Length—1¾ inches. Breadth—1½ inches. Thickness—¾ inch. Form—ovoid cuneate toward apex.

*Use.*—Market, local, dessert, culinary, canning.

*Keeping quality.*—Good.

*Resistance to insects.*—Medium.

*Resistance to diseases.*—Medium.

*Shipping quality.*—Medium.

Resembles Early Elberta in shape, J. H. Hale in color, with a ripening season a week to ten days later than Elberta.

It is understood that the foregoing characteristics are typical but subject to perhaps slight variations which may arise by reason of change of environment.

Second generation trees reproduce true to type.

I claim:

The new and distinct variety of peach tree, characterized by its extraordinary hardiness, vigorous growth, and late season of ripening, substantially as described.

MARSH HARPOLE.